United States Patent [19]

Dhadwal

[11] Patent Number: 5,155,549
[45] Date of Patent: Oct. 13, 1992

[54] METHOD AND APPARATUS FOR DETERMINING THE PHYSICAL PROPERTIES OF MATERIALS USING DYNAMIC LIGHT SCATTERING TECHNIQUES

[75] Inventor: Harbans S. Dhadwal, Westbury, N.Y.

[73] Assignee: The Research of State University of New York, Albany, N.Y.

[21] Appl. No.: 603,616

[22] Filed: Oct. 25, 1990

[51] Int. Cl.$^5$ ............................................. G01N 15/02
[52] U.S. Cl. .................................... 356/336; 356/338; 356/342
[58] Field of Search ............................ 356/335-343, 356/73, 349, 350, 73, 349, 350; 250/574, 564, 227.11, 227.16, 227.28, 227.31

[56] References Cited

U.S. PATENT DOCUMENTS

| | | | |
|---|---|---|---|
| 3,867,033 | 2/1975 | Hasinger | 356/342 |
| 4,497,577 | 2/1985 | Sato et al. | |
| 4,573,761 | 3/1986 | McLachlan et al. | |
| 4,637,683 | 1/1987 | Asawa | 356/138 |
| 4,662,749 | 5/1987 | Hatton et al. | 356/336 |
| 4,707,134 | 11/1987 | McLachlan et al. | |
| 4,768,879 | 9/1988 | McLachlan et al. | |
| 4,802,761 | 2/1989 | Bowen et al. | |
| 4,806,018 | 2/1989 | Falk | 356/446 |
| 4,848,882 | 7/1989 | Suzuki et al. | |
| 4,927,268 | 5/1990 | Carr et al. | |
| 4,934,811 | 6/1990 | Watts et al. | 356/336 |
| 4,975,237 | 12/1990 | Brown | 356/338 |
| 4,983,040 | 1/1991 | Chu et al. | 356/338 |

OTHER PUBLICATIONS

Dyott, "The fibre-optic Doppler anemometer", *Microwaves, Optics and Acoustics*, Jan. 1978, vol. 2, No. 1, pp. 13-18.

Ross et al. "The Determination of the Mean and Standard Deviation of the Size Distribution of a Colloidal Suspension . . . ", *Journal of Colloid and Interface Science*, vol. 64, No. 3, May 1978, pp. 533-542.

Auweter et al., "Fiber Optical Quasi-esastic Light Scattering of Concentrated Dispersions," *Journal of Colloid and Interface Science*, vol. 105, No. 2, Jun. 1985, pp. 399-409.

H. S. Dhadwal et al., "A fiber-optic light-scattering spectrometer," *Rev. Sci. Instrum.*, vol. 60, No. 5, May 1989, pp. 845-853.

*Primary Examiner*—Richard A. Rosenberger
*Assistant Examiner*—Hoa Pham
*Attorney, Agent, or Firm*—Hoffmann & Baron

[57] ABSTRACT

A system for determining the physical properties of materials through the use of dynamic light scattering is disclosed. The system includes a probe, a laser source for directing a laser beam into the probe, and a photodetector for converting scattered light detected by the probe into electrical signals. The probe includes at least one optical fiber connected to the laser source and a second optical fiber connected to the photodetector. Each of the fibers may adjoin a gradient index microlens which is capable of providing a collimated laser beam into a scattering medium. The position of the second optical fiber with respect to the optical axis of the probe determines whether homodyne or self-beating detection is provided. Self-beating detection may be provided without a gradient index microlens. This allows a very small probe to be constructed which is insertable through a hypodermic needle or the like into a droplet extending from such a needle. A method of detecting scattered light through the use of a collimated, Gaussian laser beam is also provided. A method for controlling the waist and divergence of the optical field emanating from the free end of an optical fiber is also provided.

32 Claims, 9 Drawing Sheets

METHOD AND APPARATUS FOR DETERMINING THE PHYSICAL PROPERTIES OF MATERIALS USING DYNAMIC LIGHT SCATTERING TECHNIQUES

This invention was made with Government support under Contract Number NCC3-172 awarded by NASA. The Government has certain rights in the invention.

BACKGROUND OF THE INVENTION

1. Field of the Invention

This invention relates to the use of dynamic light scattering (DLS) for the characterization of the structure and dynamics of such diverse systems as solids, liquid crystals, gels, solutions of biological macromolecules, electrolyte solutions, dispersions of microorganisms, solutions of viruses, membrane vesicles, protoplasm in algae and colloidal dispersions.

2. Brief Description of the Prior Art

Light scattering techniques for particle size characterization follow directly from the work of Mie in 1908 on the scattering of electromagnetic waves from dielectric spheres. The scattering depends upon particle size, wavelength, and refractive index. Techniques for particle sizing based on the angular dependence and polarization of the scattered light intensity have been routinely used to study shapes and sizes of large particles, in the Mie scattering regime. Single particle scattering systems are among some of these techniques utilizing the Mie regime. In the early 1950's it was recognized that the spectrum of the scattered light contains additional hydrodynamic properties of the scatterers, that is, translational and rotational diffusion constants. A time dependent correlation function formalism first developed by Van Hove in 1954 for neutron scattering was extended to light scattering by Komarov and Fisher in 1963. Following the invention of the laser, Pecora in 1964 showed that the frequency of the distribution of light scattered from macromolecular solutions would yield values of the macromolecular diffusion coefficient and, under certain conditions, might be used to study rotational motion and flexing of macromolecules. In 1964, Cummins, Knable and Yeh used an optical mixing technique to spectrally resolve the light scattered from dilute suspensions of polystyrene spheres. Since this pioneering work, applications have proliferated and optical mixing spectroscopy has become a major research field. Optical mixing spectroscopy is concerned with making measurements of the temporal properties of the scattered light in order to study the dynamics of the fluctuations in a fluid.

Measurement of the first order electric field autocorrelation involves elaborate optics and electronics. Direct detection (self-beating) of the scattered light leads to the second order intensity-intensity time correlation function, and homodyne or heterodyne detection leads directly to the first order electric field autocorrelation. In both cases, efficient optical mixing imposes a strict spatial coherence requirement on the optical detection system.

As discussed in U.S. Pat. No. 4,927,268, the process of obtaining particle size information by means of DLS requires relatively sophisticated optics and computer processing. However, this disclosure is not entirely correct in stating that DLS is useful for only small particles of the same size. DLS is routinely used to study highly polydisperse systems, and, also importantly, DLS provides considerably more information regarding the structure and dynamics of the system under investigation. Up until a few years ago, DLS was a specialized tool confined to a research laboratory environment with limited impact on industrial processing. However, simultaneous breakthroughs in the use of semiconductor lasers, miniaturization of the optics, avalanche photodiodes for photon counting, advances in digital electronics, and refinements in data inversion algorithms have opened up a vast area of industrial applications. DLS techniques have one other important advantage over single particle scattering systems as described by U.S. Pat. No. 4,927,268, and that is the large dynamic range over which they can operate. Single particle systems are limited to very dilute suspensions. DLS, however, can probe highly concentrated as well as very dilute systems. In particular, back scatter anemometers are even more effective in very concentrated systems. It is an object of the present invention to provide a generic multiple fiber optic probe which can be adapted to several diverse applications.

The existing state-of-art in fiber optic back scatter anemometers, which combine the transmitted and scattered laser light within the same fiber are those of Dyott [*Microwave Opt. And Acoust.*, 2, 13 (1978)] and of Auweter and Horn [*J. Colloid. and Interface Sci.*, 105, 399 (1985)]. Both types utilize a directional coupler to separate the transmitted and received signals propagating in the same sensor fiber. The transmitted beam emanates into the fluid at the full numerical aperture of the fiber, as defined in the fluid, and thus is not collimated. The back scattered signals are collected over an identical numerical aperture. In addition, the detection process is homodyne, that is, optical radiation reaching the detector comprises the sum of a local oscillator and the scattered signal. For efficient optical mixing, polarization of the two optical fields should be coincident and the wavefronts should be matched. The latter condition is easily satisfied since both optical signals travel in the same monomode fiber. The former condition is more severe and can degrade the optical mixing considerably.

One of the first uses of optical fibers in laser light scattering was described for in situ measurements of blood flow. Dyott [*Microwave Optics and Acoust.*, 2, 13 (1978)] and Ross et al. [*J. Colloid and Interface Sci.*, 64, 545 (1978)] presented a compact back scatter system for applications to particle sizing, motility, and flow measurements. This is believed to be the first portable light scattering apparatus which could be used in the field. It was also the first time that the incident laser beam and received signals were contained in a single unit. Somewhat different configurations have been described by Auweter and Horn [*J. Colloid and Interface Sci.*, 105, 309 (1985)]. Dhadwal and Chu [*App. Opt.*, 28, 411 (1989)] demonstrated the use of an optimized fiber optic receiver for both dynamic and static light scattering. In all the above cases a single fiber has been utilized in the composite probe. Dhadwal and Chu made a compact light scattering spectrometer using many single fiber/GRIN microlens probes.

SUMMARY OF THE INVENTION

It is an object of the invention to provide an optical probe which is suitable for dynamic light scattering studies of diverse systems. The temporal properties of the scattered light can thereby be predicted from the first order electric field autocorrelation.

It is another object of the invention to avoid the use of a fiber directional coupler by assigning one or more optical fibers for transmitting an optical field to a scattering medium and using several optical fibers for receiving the scattered signal. The purpose of utilizing a plurality of optical fibers is to provide simultaneous filtering of the scattered light at different scattering angles. In accordance with another object of the invention, a quarter pitch gradient index (GRIN) microlens is used to transmit a collimated laser beam to the scattering region and to receive the scattered light.

In accordance with these and other objects of the invention, a system is provided which includes a probe body, a first optical fiber secured to the probe body, and a second optical fiber secured to the probe body. Means are provided for directing a laser beam into the first optical fiber. The first and second optical fibers each include a free end. The free ends of these fibers adjoin a quarter pitch, gradient index microlens. A laser source is provided for directing a laser beam into the first optical fiber. The beam passes through the microlens such that a collimated beam can be introduced into a scattering medium. Photodetecting means are connected to the second optical fiber. The second optical fiber may be positioned at the mirror image of the first optical fiber to provide homodyne detection. The second optical fiber may alternatively be positioned at a point which is not symmetrically located about the optical axis of the probe in order to provide self-beating detection.

A system requiring no gradient index microlens while providing efficient, self-beating detection is also provided. The system includes first and second optical fibers, means for causing a laser beam having a Gaussian distribution to emanate from a free end of the first optical fiber, detecting means connected to the second optical fiber, and a probe body to which the free ends of the first and second optical fibers are secured. The second optical fiber includes a free end positioned at a selected scattering angle so that it can function as a self-beating receiver. Additional optical fibers may be positioned relative to first optical fiber in order to define a range of scattering angles. However, using commercially available optical fibers, and taking into account the size of the probe, a back scatter probe with a scattering angle of about 157° was found to be optimum. Additional control of the waist and divergence, with use of additional optical components, of the Gaussian beam emanating from the free end of the fiber may permit a scattering angle close to 180°.

A method of detecting scattered light is also provided by the invention. The method includes the steps of providing a probe including a probe body, a first optical fiber secured to the probe body, a second optical fiber secured to the probe body, a quarter pitch, gradient index microlens having a front face and a back face, the first and second optical fibers including free ends adjoining the front face of the quarter pitch, gradient index microlens, inserting the probe into a scattering medium, transmitting a laser beam through the first optical fiber and into the scattering medium, and transmitting light scattered by the scattering medium through the second optical fiber. The quarter pitch, gradient index microlens transforms the beam emanating from the first optical fiber into a collimated laser beam.

Other objects and advantages of the systems disclosed herein will become apparent from the detailed description which follows.

DETAILED DESCRIPTION OF THE INVENTION

1. Temporal Correlations for Brownian Motion

The derivation of the theoretical model derived in the study of Brownian motion and self-propelled organisms is possible by assuming that the scatterers are point sources and move independently of each other. For plane coherent monochromatic light of constant intensity incident on a collection of particles, the total scattered electric field in the direction Θ is $$E_s(t) = \sum_{m=1}^{N} E_m^0 \exp(j(\Phi_m(t) - \omega_o t)) \tag{1}$$

where $E_m^0$ is the amplitude of the scattered electric field due to the m'th particle and is a function of the particle radius, scattering angle and refractive index, $\Phi_m(t)$ is the instantaneous phase of the scattered field at time t due to the m'th particle and indicates the precise position of the particle, $\omega_o$ is the angular frequency of the incident optical wavefield and $j=\sqrt{-1}$.

The unnormalized first order electric field correlation for the scattered field is $$c(\tau) = <E_s^*(t)E_s(t+\tau)> \tag{2}$$

where * denotes the complex conjugate and $<.>$ denotes a temporal average. Substituting equation (1) into (2) gives $$c(\tau) = <\sum_{m=1}^{N}\sum_{n=1}^{N} E_m^o E_n^o \exp[j(\Phi_m(t+\tau) - \Phi_m(t))]> \tag{3}$$

In the above expression the summation is over all the particles of the scattering ensemble. The phase of the field due to the m'th particle is $$\Phi_m(t) = Q \cdot r_m(t) \tag{4}$$

where $r_m(t)$ is the position vector of the m'th particle at time t and the Bragg vector Q is related to the scattering angle according to $$|Q| = \frac{4\pi n}{\lambda_o}\sin\left(\frac{\theta}{2}\right) \tag{5}$$

where n is the refractive index of the host medium and $\lambda_o$ is the free space wavelength of the incident optical wavefield.

In general, equation (1) is only applicable to particles which are small compared with the wavelength of light. If L is the maximum dimension of the particle then $_4 Q L < 1$. For back scatter this gives an upper limit of 0.15 $\mu$m. However, it has been found that in practice the size of the particle may be considerably larger before diffraction effects due to particle size become significant.

If the particles are assumed to be identical, that is, $E_m^o = E_n^o = E^o$, and the contribution from the m'th and n'th particle are statistically independent, then equation (3) reduces to:

$$\begin{aligned}c(\tau) &= N|E^o|^2 <\exp[j(\Phi(t+\tau) - \Phi(t))>\\ &= N|E^o|^2 <\exp[j(Q \cdot r(t+\tau) - Q \cdot r(t))>\\ &= N|E^o|^2 <\exp[jQ \cdot r'(\tau)]>\end{aligned} \tag{6}$$

where $r'(\tau) = r(t+\tau) - r(t)$. If $v(t)$ is the velocity of the particle at time t then $$r'(\tau) = \int_0^\tau v(t)dt$$

Hence $$c(\tau) = N|E^o|^2 <\exp\left[jQ \cdot \int_0^\tau v(t)dt\right]> \tag{7}$$

The entire problem now rests in evaluating the expectation on the right hand side of equation (7). For brownian motion, equation (7) reduces to:

$$c(\tau) = N|E^o|^2 \exp(-Q^2 D^o \tau) \tag{8}$$

where $D^o$ is the translation diffusion coefficient at infinite dilution and is related to the frictional coefficient, f, through the Stokes-Einstein relation $$D^o = \frac{kT}{f} \tag{9}$$

where k is Boltzman's constant and T is the absolute temperature. In the case of spherical particles of radius a $$f = 6\pi\eta a \tag{10}$$

where $\eta$ is the intrinsic viscosity of the host medium.

If the particles in suspension are not identical, then equation (8) has to be modified to account for the spread in sizes. Assuming that N(a) is the number distribution in particle radius, then the electric field autocorrelation function becomes, $$c(\tau) = \int_0^\infty N(a)|E^o|^2 \exp\left[-\frac{Q^2 kT}{6\pi\eta a}\tau\right]da \tag{11}$$

By defining a laser light scattering size distribution, $f(a) = N(a)|E^o|^2$ the autocorrelation function becomes $$c(\tau) = \int_0^\infty f(a)\exp\left[-\frac{Q^2 kT}{6\pi\eta a}\tau\right]da \tag{12}$$

It is common practice to use the substitution $$\Gamma = \frac{Q^2 kT}{6\pi\eta a}$$

to rewrite the above equation in the normalized form $$g^{(1)}(\tau) = \int_0^\infty G(\Gamma)e^{-\Gamma\tau}d\Gamma \tag{13}$$

where $G(\Gamma)$ is known as the characteristic linewidth distribution function. The inversion equation (13), Laplace transform inversion, has been the subject of numerous studies and is the first step in the inversion of experimental measurements of the scattered light autocorrelation function before the size distribution or the molecular weight distribution can be determined.

The particle size distribution, N(a), can be determined from the characteristic linewidth distribution, $G(\Gamma)$ using the following transformations. Firstly, the laser scattering distribution, f(a) is computed given the temperature, T in degrees Kelvin, the intrinsic viscosity $\eta$ in Kg. $(\mu m)^{-1}$. sec.$^{-1}$, and refractive index of the solvent. The abscissa of $G(\Gamma)$ are scaled by using $$a = \frac{KTQ^2}{6\pi\eta}\cdot\frac{1}{\Gamma}$$

where a is the particle radius in microns, $Q(\mu m.^{-1})$ is the Bragg vector as defined by equation f(5) and the Boltzman's constant $k = 1.38 \times 10^{-111}$ Kg. $(\mu m)^2 \sec^{-2}$. The ordinates are scaled to give $$f(a) = \Gamma^2 G(\Gamma)$$

Now if the scattering amplitude $|E^o|^2$, the particle radius, the ratio of the particle to solvent refractive index, and the scattering angle are known, then we can scale the abscissa of f(a) to give the particle size distribution, N(a) by $$N(a) = \frac{f(a)}{|E^o|^2}$$

Intermediate distributions should be normalized to unity area before applying the appropriate scaling factors.

2. Self-Propelled Motion—Spermatozoa and Bacteria

For particles with linear velocities that remain unchanged over the measurement time relevant to the scattering experiments, the phase integral in equation (7) reduces to $$\int_0^T v(t)dt = vT$$

where the velocity of the particle is maintained over distances that are long compared with $\bar{Q}^1$. In the absence of external forces and assuming an isotropic velocity distribution, evaluation of the expectation $<>$ in equation (7) gives $$g^{(1)}(\tau) = \int_0^\infty \frac{\sin(Qv\tau)}{Qv\tau} P_s(v)dv \quad (14)$$

where $P_s(v)$ is the distribution of swimming speeds to be recovered from measured correlation functions.

3. Spatial Coherence Considerations—The Diffraction Approach

One of the essential components of a successful dynamic light scattering apparatus is the detector module, which usually includes a series of distributed optical elements placed outside the scattering cell. The lenses and pinholes are arranged to define a certain angular uncertainty (or resolution) and an effective entrance pupil. The effectiveness of the detector assembly for DLS is measured by the light beating to shot noise ratio (more commonly referred to as the spatial coherence factor, $\beta$). It is now standard practice to design the detector module so that the ratio of the coherence area to the detector area is less than unity. However, the derivation of the spatial coherence requirements is based on a treatment of the scattering volume as a quasimonochromatic two dimensional spatially incoherent source, whose area is a projection of the scattering volume in a plane perpendicular to the direction of observation. The latter condition ensures that the coherence area is independent of the scattering angle. In actuality, the scattering volume is a three dimensional source and at least one of the three dimensions could change with the scattering angle. The coherence area is usually expressed as a product of the coherence solid angle, $\Omega_{coh}$ and the square of the distance between the scattering center and the detector. There are several known ways of deriving expressions for the coherence solid angle by treating the scattering volume to be a three dimensional source. In a rectilinear coordinate system, consider the propagation of a linearly polarized, in the x-direction, laser beam in the z-direction and that the scattering is confined to the y-z plane. Derivation of $\Omega_{coh}$ can be divided into two planar coherence angles $(\Delta\Theta)_{coh}$ and $(\Delta\phi)_{coh}$ in the y-z and x-$k_s$ planes, respectively—where $k_s$ is the scattering vector. The diffraction approach for computing the coherence angles is based on the fact that coherence vanishes when relative phases of the waves reaching the observer from any two points on the extended source changes by an amount $\pm\pi$ as the observer moves from a position of perfect coherence to that of complete incoherence. The source points that produce the maximum relative phase change are determined by the extremal dimensions of the source as seen by the observer. In DLS, an incident laser beam has a circular cross-section of diameter, $D_I$, and the length, $L_z$, of the scattering volume is a function of the scattering angle. In general, the shape of the scattering volume formed by two intersecting cylinders is some solid ellipsoid, which approaches a parallelepiped, for $D_I < D_A$, where $D_A$ is the diameter of the interrogating detection beam. By considering the total relative phase arising from two extremal points in the scattering region, an expression for the planar coherence solid angle can be derived:

$$(\Delta\theta)_{coh} = \frac{\lambda\sin^2(\theta)}{2[D_A + D_I\cos(\theta)]} \quad (15)$$

4. Fiber Optic Probes for the Back Scatter Regime

Figures 1, 1A:
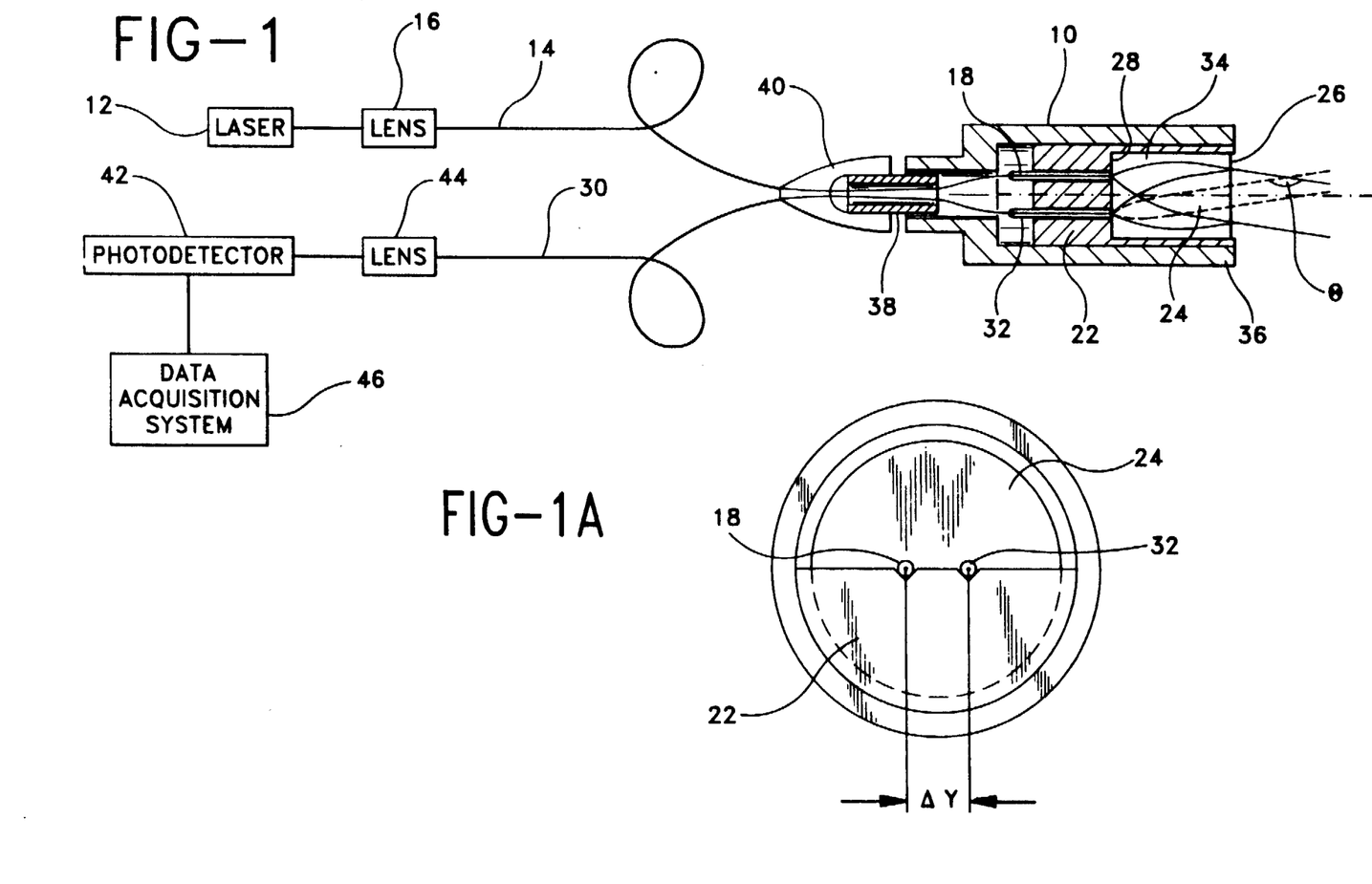
FIG. 1 is a schematic illustration of a dynamic light scattering detection system including a back scatter probe utilizing homodyne detection in connection with the invention.
FIG. 1A is an enlarged, front elevation view of the probe shown in FIG. 1.

FIG. 1 shows a compact back scatter optical probe 10 which combines the delivery of a Gaussian laser beam to a scattering medium and a homodyne receiver system in a single compact optical head. In this embodiment of the invention, a quarter pitch, graded index (GRIN) microlens is used to separate the transmitted and detected beams, as opposed to a fiber directional coupler. The GRIN microlens also provides additional control of the size of the scattering volume.

Light from a laser source 12 is launched into a polarization maintaining monomode optical fiber 14 by means of either a GRIN microlens 16 or a microscope objective. The other end of the optical fiber is mounted into a glass capillary 18 (alternatively a stainless steel ferrule or any other suitable material), which is actively aligned by means of V grooves 20 in a brass ferrule 22. A quarter pitch GRIN microlens 24 epoxied into the ferrule 22 transforms the light emanating from the fiber mounted in the lass capillary 18 into a collimated laser beam at the output face 26 of the GRIN microlens. The waist, $\omega_o$ is related to the input waist $\omega_i$, which is equivalent to the core radius of the optical fiber 14 by the relation $$\omega_o = \frac{\lambda}{\pi N_o \sqrt{A} \; \omega_i}$$

where $N_o$ and $\sqrt{A}$ are the axial index of refraction and the quadratic index constant of the microlens, respectively, and $\lambda$ is the wavelength of light. The divergence angle of the Gaussian beam is given by $$\theta = \frac{\lambda}{\pi\omega_o}$$

The front face 28 of the GRIN microlens 24 is antireflection coated but the back face 26 is not antireflection coated. Consequently, the back face 28 acts like a partial mirror, thereby providing a diminished image of the input fiber at a point symmetrically located about the optical axis. An optical fiber 30 mounted to a glass capillary 32 positioned at this location will receive the back reflected signal 34 from face 26 together with the back scattered signal from particles near the tip of the probe body 36. A monomode, polarization maintaining fiber is preferred for homodyne detection. The two fibers are epoxied into a bushing 38, which fits into the probe body 36, and a heat shrinkable tube 40 is used to relieve strain on the fibers. The back reflected and scattered signals are guided to a photodetector 42 by another polarization maintaining fiber 30 and a GRIN microlens 44. The photogenerated current at the output of a suitable photodetector is processed by a data acquisition system 46 to give the normalized first order autocorrelation of the scattered light.

The composite probe is no more than 5 mm. in diameter and 50 mm. in length. The scattering angle $\Theta$ is given by $$\theta_s = (\pi - N_o \sqrt{A}\ \Delta y) \pm N_o \sqrt{A}\ \omega_i$$

where $\Delta y$ is the separation between the two glass capillaries 18 and 32, and $\omega_i$ is radius of the core of the optical fiber 30. The choice of the GRIN microlens 24 and a detector fiber 30 are dictated by the strict spatial coherence requirement discussed earlier.

Figures 2, 2A:
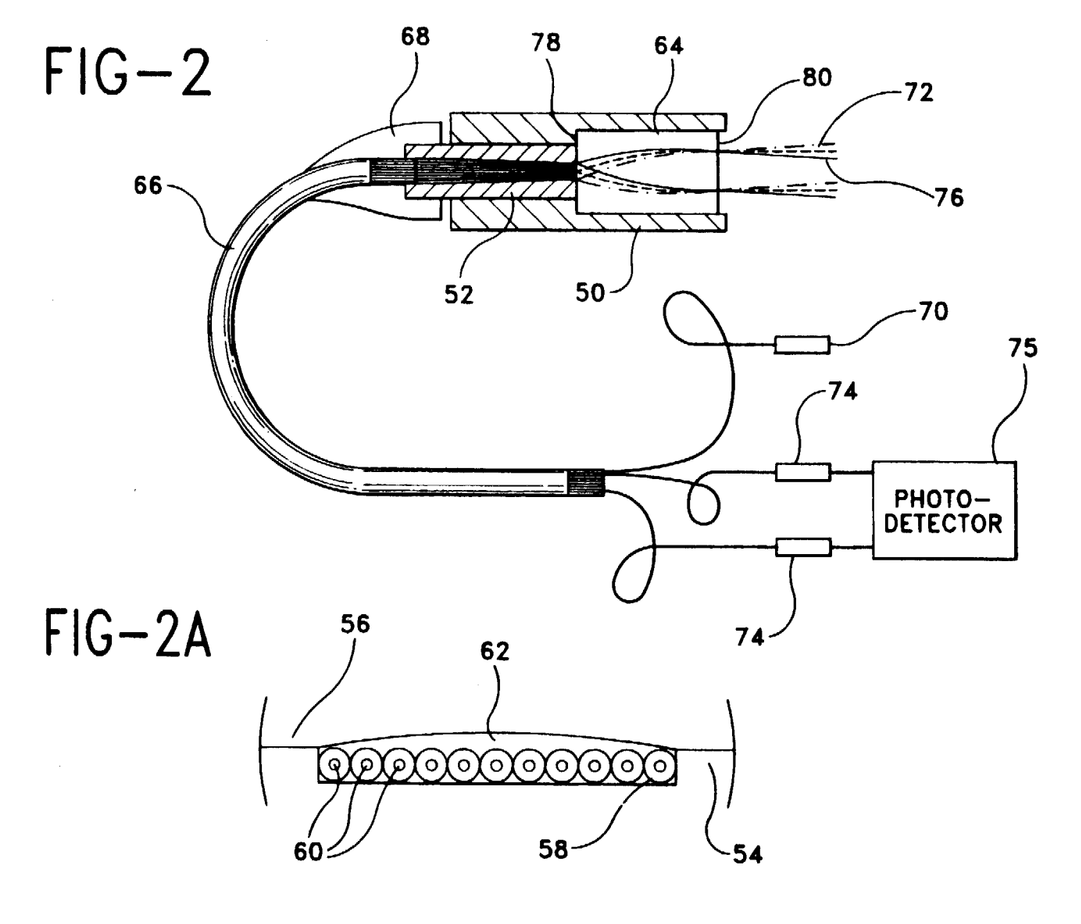
FIG. 2 is a schematical illustration of a back scatter probe utilizing both homodyne and self-beating detection in connection with the invention.
FIG. 2A is an enlarged, schematical illustration of a linear array of optical fibers positioned in the front focal plane of a GRIN microlens as shown in FIG. 2.

FIGS. 2 and 2A show a multiple fiber back scatter probe 50. A linear array of eleven optical fibers is formed onto brass ferrule 52 comprising lower 54 and upper 56 portions. One of the fibers 58 is a monomode optical fiber which is used for delivering light from a laser source to the scattering medium by means of a quarter pitch GRIN microlens. The other ten optical fibers 60 are identical and have a core diameter of eight microns, which makes them multimode at the wavelength of operation. The fibers are held in position by means of epoxy 62. The fiber array mounted in the ferrule 52 is positioned in the back focal plane of the quarter pitch GRIN microlens 64 which is mounted in the probe body. The eleven fibers are grouped into a cable 66 which is secured to the probe ferrule 52 with a heat shrinkable tube 68. As above, light from a laser source is launched into the transmitting fiber by means of a suitable lens 70. Fibers 60 adjacent to the transmitting fiber 58 receive the scattered signal 72, which is transmitted to the photodetector 75 by means of the optical fibers and quarter pitch microlenses 74. The scattering angle for the p'th fiber as measured from the transmitting fiber is given by $$(\theta_s)_p = [\pi - N_o \sqrt{A}\ p\Delta y] \pm N_o \sqrt{A}\ r_f,\ p = 1,2,3,\ldots,10$$

where $r_f$ is the core radius of the receiving optical fiber ($=\omega_i$ for the receiving fiber), and $\Delta y$ is the separation between the fibers in array. The waist of the transmitted laser beam 76 is $$\omega_o = \frac{\lambda}{\pi r_f'} \frac{1}{N_o \sqrt{A}}$$

where $r'_f$ is the core radius of the transmitting fiber. In this configuration the front 78 and back 80 surfaces of the microlens 64 are both antireflection coated, thereby reducing the amount of flare in the microlens. Flare reduces the self-beating efficiency of the detection process and should be avoided. The second through tenth fibers 60, together with the GRIN microlens, provide a self-beating detection system. Multimode fibers are preferred for self-beating detection. The eleventh fiber 60, which is located at the mirror image of fiber 58, provides homodyne detection because of the additional back reflection component from the back surface 80.

Both the above configurations of a back scatter anemometer for dynamic light scattering have unique distinguishable features that the current state-of-art systems do not possess. Firstly, the costly directional coupler has been eliminated. Secondly, homodyne and self-beating measurements of the scattered light can be performed over a range of angles from 156° to 177.6° by means of a single probe with a resolution of 2.4°±0.08°. Thirdly the use of a quarter pitch GRIN microlens allows the delivery of a collimated laser beam to the scattering system. Self-beating measurements, which were not possible within the same probe body until the present invention, are usually preferred over homodyne schemes.

Figure 3:
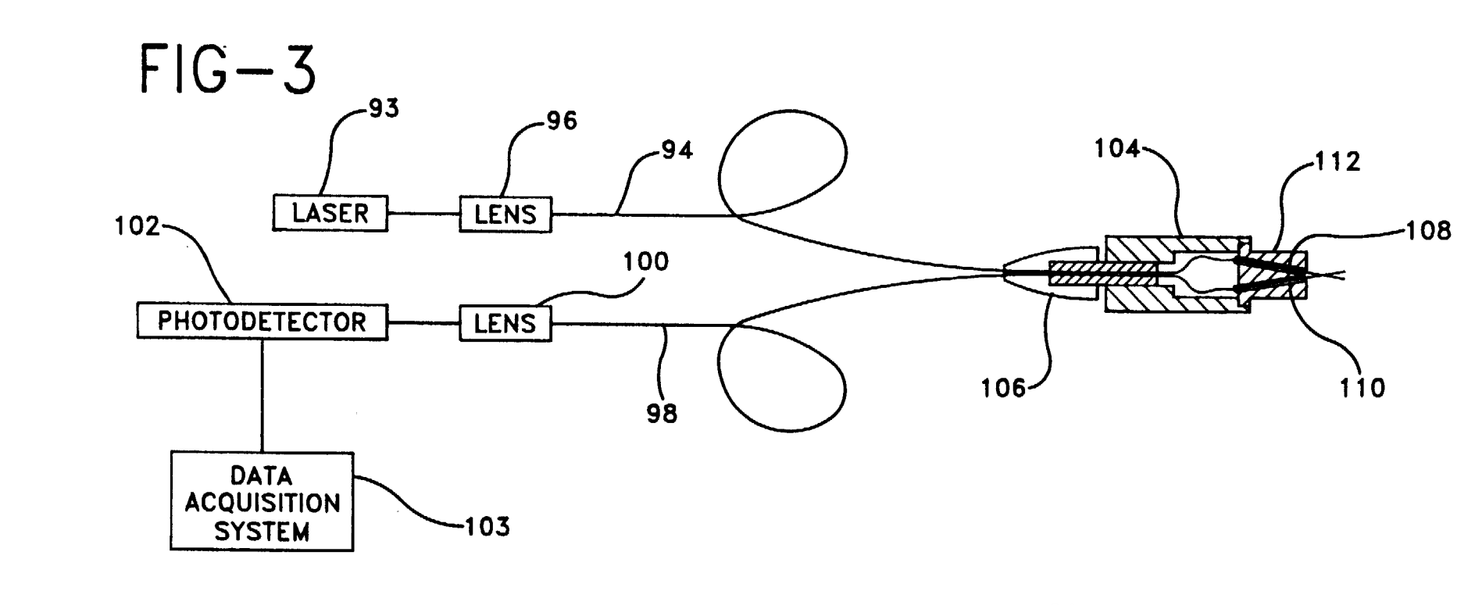
FIG. 3 is a schematic illustration of a system including a back scatter probe utilizing self-beating detection.
Figure 3A:
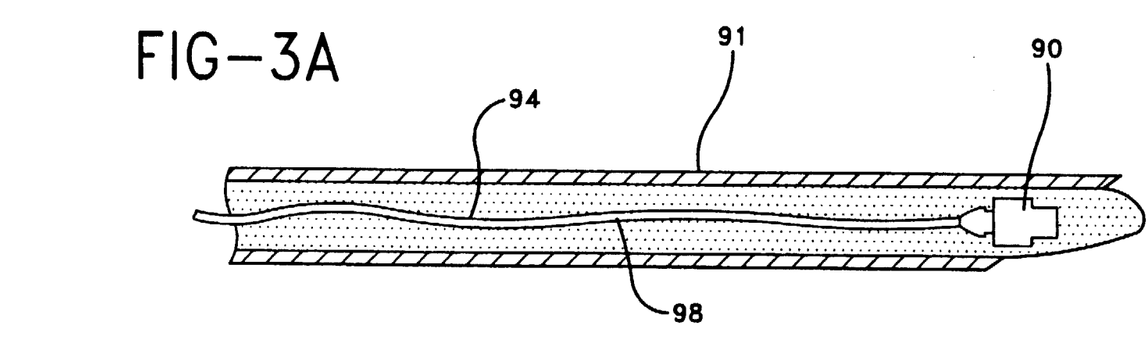
FIG. 3A is an enlarged, sectional elevation view of the probe shown in FIG. 3 positioned within a droplet formed at the end of a needle.

The back scatter probe 90, shown in FIG. 3, does not require the use of a GRIN microlens or any other lens. Realization of this configuration follows from consideration of the spatial coherence requirements as discussed previously. For efficient self-beating detection, the scattering region, which is a three dimensional volume source, must have the magnitude of the complex degree of coherence $|\gamma_{12}(\tau')|$ as close as possible to unity. In the extreme limits a point scattering region or alternatively a point detector both satisfy this condition, but neither is possible. In practice, then, the coherence requirements translate into approaching this condition. However, another conflicting requirement is that of the need for a finite scattering volume in order to observe the scattering process, that is the value of unity for $|\gamma_{12}(\tau')|$ may not be desirable. The size of the scattering volume and the size of the detector are coupled together; the effects of both cannot be independently assessed. Based on the analysis presented previously, the coherence angle (equation (15)) approaches a maximum value at a scattering angle of 90° and zero in the forward and back scattering regions ($\Theta=0,\pi$). In a conventional light scattering spectrometer, a laser beam is focussed into the scattering region by means of a convex lens to produce a waist size in the range of 100 to 200 microns. Stronger focussing, though desirable, can lead to distortions in the measured correlation function, because the length of the scattering region seen by a conventional detection system is usually much larger than the incident beam diameter (alignment is easier). Consequently the phase curvature leads to pronounced distortions in the forward direction. The laser beam profile emanating from the end of a monomode fiber (at $\lambda=475$ nm. in water) has a Gaussian distribution with a waist of 4 microns, which gives a coherence solid angle, using equation (15), of 13.5 mrad. at a scattering angle of 150° and a coherence solid angle of 6 $\mu$rad. at a scattering angle of 179°. An optical fiber with a waist size of 4 $\mu$m. in water has an acceptance angle of 39 mrad. This means that a back scatter probe using two optical fibers without a GRIN microlens will give an efficient self-beating detection system. An additional advantage will be the extremely small size of the subsequent probe, less than 0.5 mm in diameter. This has considerable significance in the study of DLS probes for a microgravity environment. For example, the growth of protein crystals in a microgravity environment involves suspending droplets from hypodermic needles. Using this embodiment of the invention, it will be possible to insert the above probe through the needle 91 into the droplet and monitor the kinetics of the crystallization process, in situ, as shown in FIG. 3A.

Figure 4:
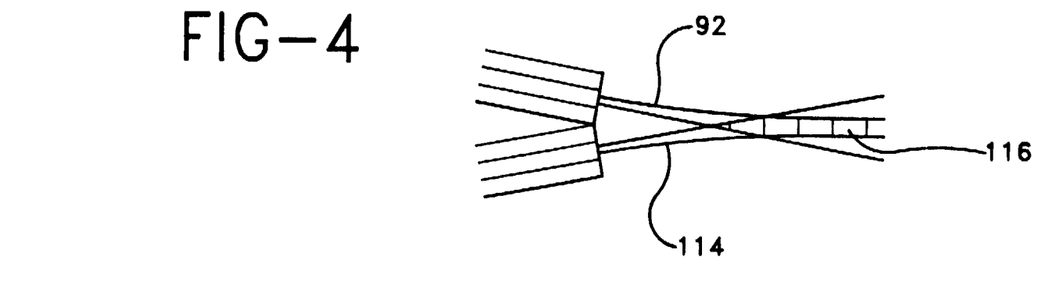
FIG. 4 is a schematical illustration of the intersection of the incident beam from a monomode fiber shown in FIG. 3 and the numerical aperture of a detection fiber.

In FIGS. 3–4, a laser beam 92 from a laser source 93 is delivered to the scattering region by means of a monomode optical fiber 94, and a launching lens 96. The scattered signal is detected by means of a multimode optical fiber 98, a GRIN lens 100 and a photodetector 102. The photodetector is connected to a data acquisition system 103. In this configuration, a probe body 104 is shown in unnecessarily more complexity than required. (The optical fibers may simply be epoxied to a wedge so that they are properly oriented with respect to each other). Bushing 106 attaches the two fibers 94 and 98 to the probe body 104. The fibers are terminated in glass ferrules 108 and 110 and mounted in a holder 112, which is attached to probe body 104. The incident beam 92 has a Gaussian profile as described earlier, and consequently the detection fiber collects scattered light over a range of scattering angles defined by the numerical aperture 114 of the multimode fiber 98. The scattering region 116 is defined by the intersection of beam 92 and aperture 114.

Figure 5:
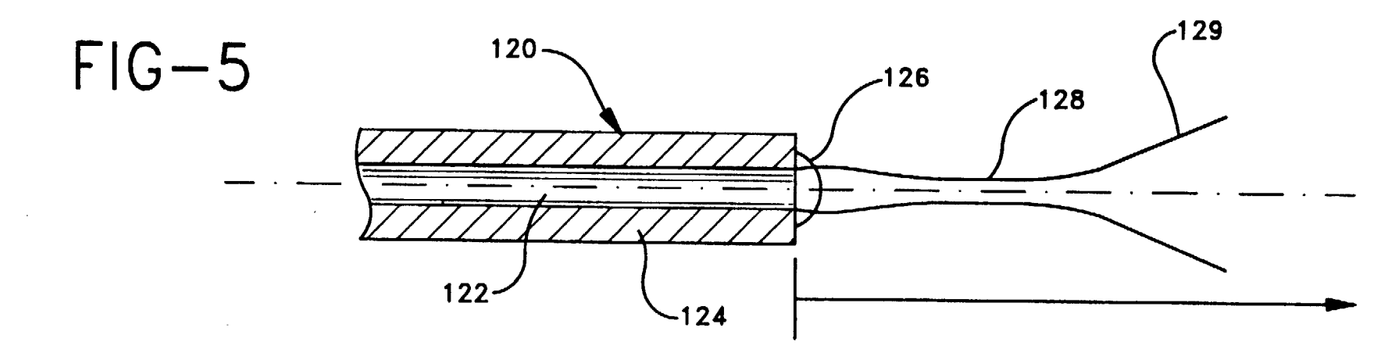
FIG. 5 is an enlarged schematical illustration of a microlens on the tip of an optical fiber.

Additional control of the beam waist of the laser light emanating from the monomode fiber of probe 90 may be controlled by fabricating a microlens on the tip of the fiber as shown in FIG. 5. This gives additional flexibility for optimization of optical probes for particular applications. In FIG. 5, a monomode fiber 120 has a core region 122 which supports a Gaussian laser beam, and a cladding region 124 which is much larger than the core. A microlens 126 is formed on the end of the monomode fiber by dipping the fiber end into a negative photoresist while the fiber core carries $> =0.1$ mw of He-Ne laser light. The desired waist 128 of the transmitted laser beam can be produced by multiple dips and actively monitoring the laser beam radiation pattern 129.

Figure 5A:
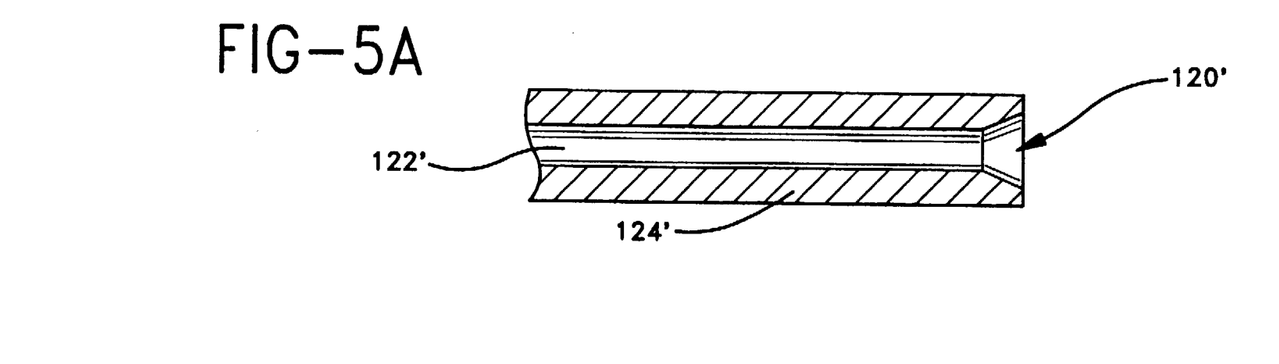
FIG. 5A is an enlarged schematical illustration of the free end of a monomode fiber having an expanded core portion.

A second method for controlling the characteristics of the optical wavefield emanating from the tip of the fiber involves heating of the fiber end such that the core of the fiber diffuses into the cladding region. This results in a flaring of the effective mode volume near the tip of the fiber, thereby increasing the effective waist, and reducing the divergence of the transmitted laser beam. An optical fiber 120' as shown in FIG. 5A is particularly suitable for a probe as shown in FIG. 3. The flaring of the core 122' near the tip of the fiber through diffusion into the cladding material 124' reduces beam divergence, and allows the transmitting fiber to be oriented more closely to parallel with the receiving fiber than the arrangement shown in FIG. 3. This allows the probe to be even smaller.

Figure 6:
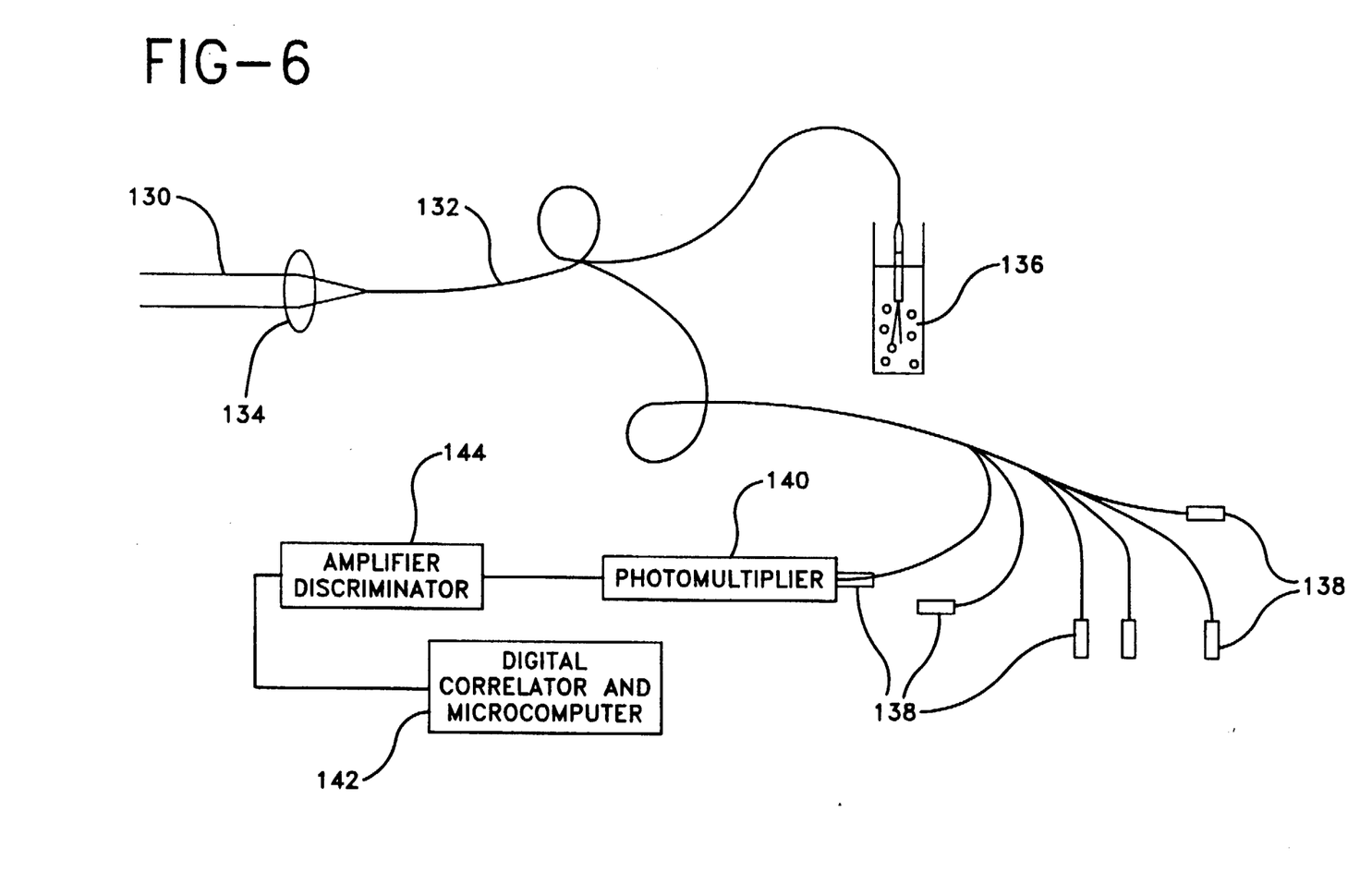
FIG. 6 is a schematical illustration of an optical system used for testing fiber optic probes.

Fiber optic probes described above can be tested by employing the optical system shown in FIG. 6. A laser beam 130 from a Spectra Physics He-Ne (SP124B) laser is launched into a transmitting optical fiber 132 by means of 20×microscope objective 134. An aqueous suspension 136 of 0.176 μm nominal diameter latex spheres with a concentration of ≃ $-8$ g/ml. may be used to evaluate the accuracy of particle sizing. The free ends of the optical fibers used as receivers are terminated using SMA type 2 connectors 138 and coupled to the face plate photomultiplier housing 140 by employing a quarter pitch GRIN microlens. An interference filter (not shown) is positioned within the face plate and in front of a photocathode. A digital correlator 142 is used to measure the intensity-intensity correlation function, $G^{(2)}(\tau)$ for each of the three fiber optic probes described above. An amplifier discriminator 144 is connected between the digital correlator and photomultiplier. In a commercial unit, semiconductor lasers and photon detectors may be employed to gain considerable cost and size reduction.

The photomultiplier 140 produces at its output a train of photo-electron pulses n(t), which is proportional to the instantaneous intensity of the optical radiation reaching the photocathode surface. The photon correlator measures photon correlation $<n(t)n(t+\tau)>$, which is proportional to the intensity-intensity time correlation $G^{(2)}(\tau)$. In general, the instantaneous photon count rate n(t) has two components, one corresponding to the coherent addition of field amplitudes arising from different points within the scattering volume and the second corresponding to the incoherent addition of the field amplitudes. The ratio of the coherent component to the total count rate is a measure of the magnitude of the complex degree of coherence, which represents the self-beating efficiency. Thus, the spatial coherence factor $\beta'$ is defined by $$\beta' = |\gamma_{12}(\tau')| = \frac{I_{coh}}{I_{tot}} = \frac{<n_s>}{<n>}$$

where $<n_s>$ and $<n>$ are scattered photon signal and total count rates, respectively. By considering the optical signal reaching the photomultiplier to contain a local oscillator signal $\eta/_o$, the unnormalized intensity-intensity time correlation function is given by $$G^{(2)} <\eta>'^2 + 2<n_s>\eta/_o g^{(1)}(\tau) + <\eta_x>^2 |g^{(1)}(\tau)|^2$$

where $<n>' = <n> + n_{/o}$, $g^{(1)}(\tau)$ is the normalized first order electric field correlation. Normalization with the baseline $<n>'^2$ gives $$G^{(2)}(\tau) = \frac{G^{(2)}(\tau)}{<n>'^2} - 1$$

$$= 2\beta' \frac{n_{lo}}{<n>'} g^{(1)}(\tau) + \beta'^2 |g^{(1)}(\tau)|^2$$

Figure 7:
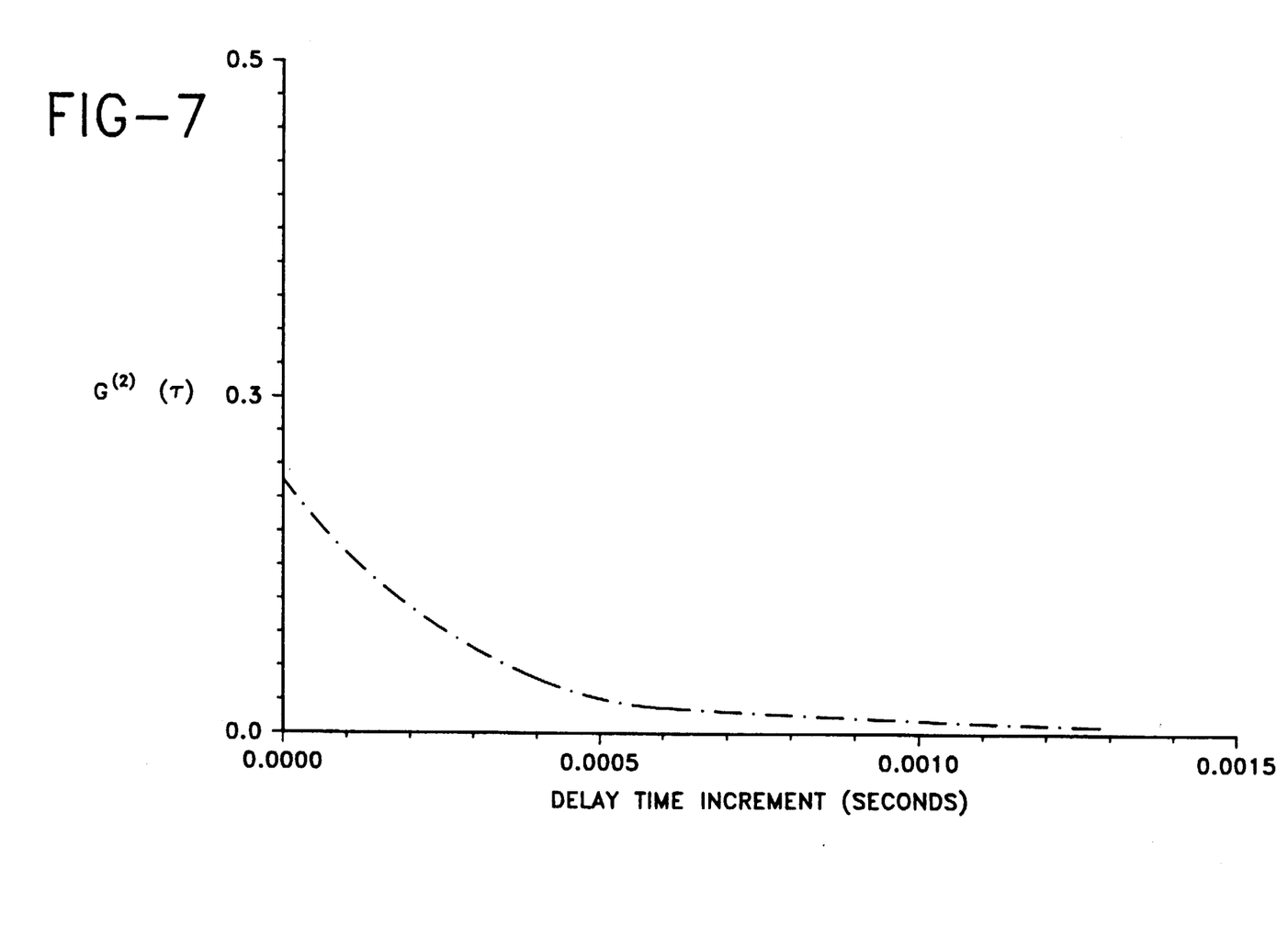
FIG. 7 is a graph illustrating the normalized intensity-intensity time correlation function obtained using the fiber probe illustrated in FIG. 1.
Figure 8:
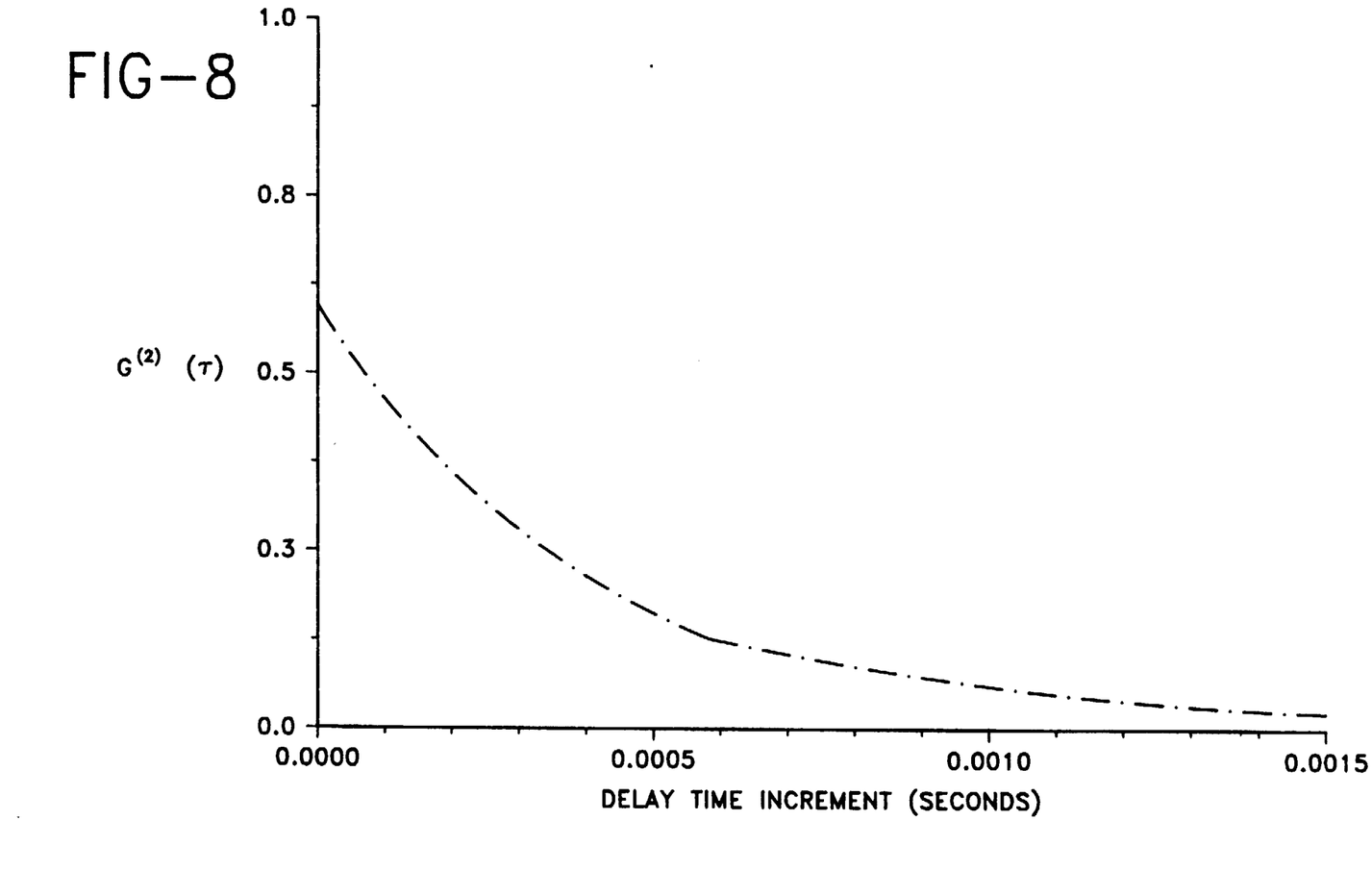
FIG. 8 is a graph illustrating the normalized intensity-intensity time correlation function obtained using the fiber probe illustrated in FIG. 2.
Figure 9:
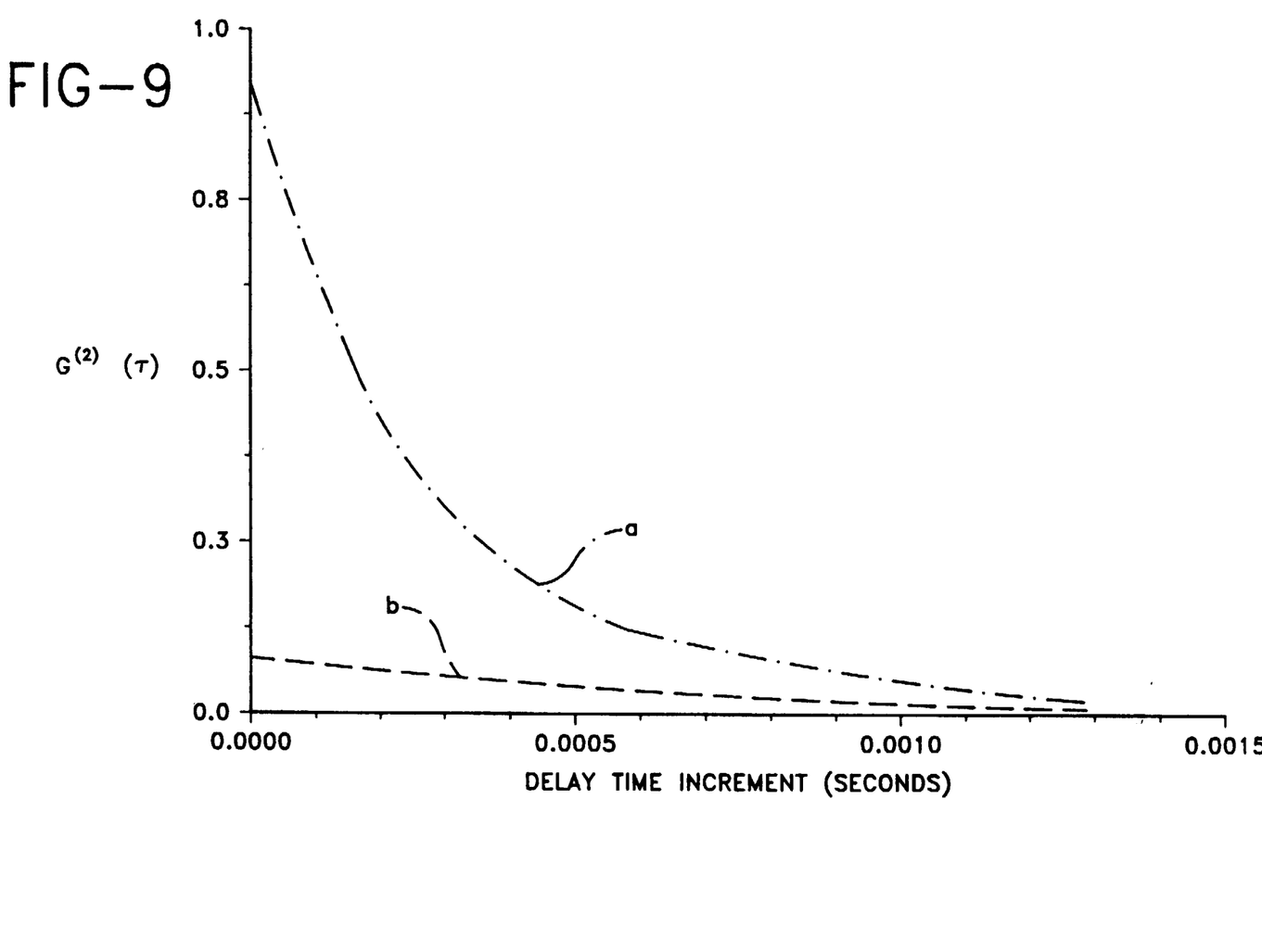
FIG. 9 is a graph illustrating the normalized intensity-intensity time correlation function obtained using the fiber probe illustrated in FIG. 3 (curve a). Curve b shows the lack of spatial coherence when a back scatter probe with two monomode optical fibers positioned side by side is used.

For a self-beating experiment, $\eta/o=0$, the first term in the above equation goes to zero giving the Siegert relation. For a homodyne detection with $<n_s> << <n_{/o}>$, the second term in the above equation vanishes. FIGS. 7, 8, and 9 show the subsequent intensity-intensity correlation function measured using the probes described in FIGS. 1, 2, and 3, respectively. The intercept of these curves gives the self-beating efficiency parameter, $\beta'$, which is largest for probe 90 and is approaching the theoretical limit of unity. In FIG. 9, curve (a) corresponds to probe 90 in FIG. 3 with $\Delta\Theta=23°$, curve (b) represents measurements of $G^{(2)}(\tau)$ with a back scatter probe comprising two monomode fibers positioned side by side ($\Delta\Theta=0$). This demonstrates, as discussed above, the poor light beating efficiency, and as such this latter probe is unsuitable for DLS. The design of probe 90 accordingly involves considerable understanding of the spatial coherence requirements.

The correlation data described above is analyzed using a non-linear least squares curve fitting procedure based on the method of cumulants. Estimates of particle size and $\eta'$ are summarized in Table 1. $\beta'$ is preferably at least about 0.5.

TABLE 1

| Analysis of correlation data in FIGS. 7, 8, and 9 | | | |
|---|---|---|---|
| Probe | Θ | Diameter (nm) | $\beta'$ |
| 10 | 161.0 | 161 | 0.77 |
| 50 | 177.6 | 178 | 0.45 |
| 90 | 157.0 | 193 | 0.96 |

OTHER APPLICATIONS

The accuracy of fiber probes 10, 50, and 90 can be demonstrated by measuring the size of polystyrene spheres. However, these probes can be used for measurements of the swimming speed distribution of microorganisms such as bacteria. There are several other applications of the multiple fiber probe described above. Some of these are discussed below.

Measurements of the scattered light intensity at closely packed forward angles is very important. This can be achieved with conventional spectrometers using a single fiber probe. However, the ability to have a single fiber probe providing a parallel filtering of the scattered optical wavefield prior to detection will be a very significant addition and improvement to existing techniques. For example, the back scatter probe described above can be used in the forward region without any changes. In this region the multiple fiber probe acts as a composite receiver. However, incident laser light must be introduced into the scattering region by other means. The angular separation, 2.4° for the probe described above, and the total range can be improved substantially by using a smaller separation between the fibers and a large number of fibers, respectively. It should be noted that while a linear array of fibers is employed in the above-described example, any other coplanar arrangement of the free ends of the fibers can alternatively be utilized.

Figure 10:
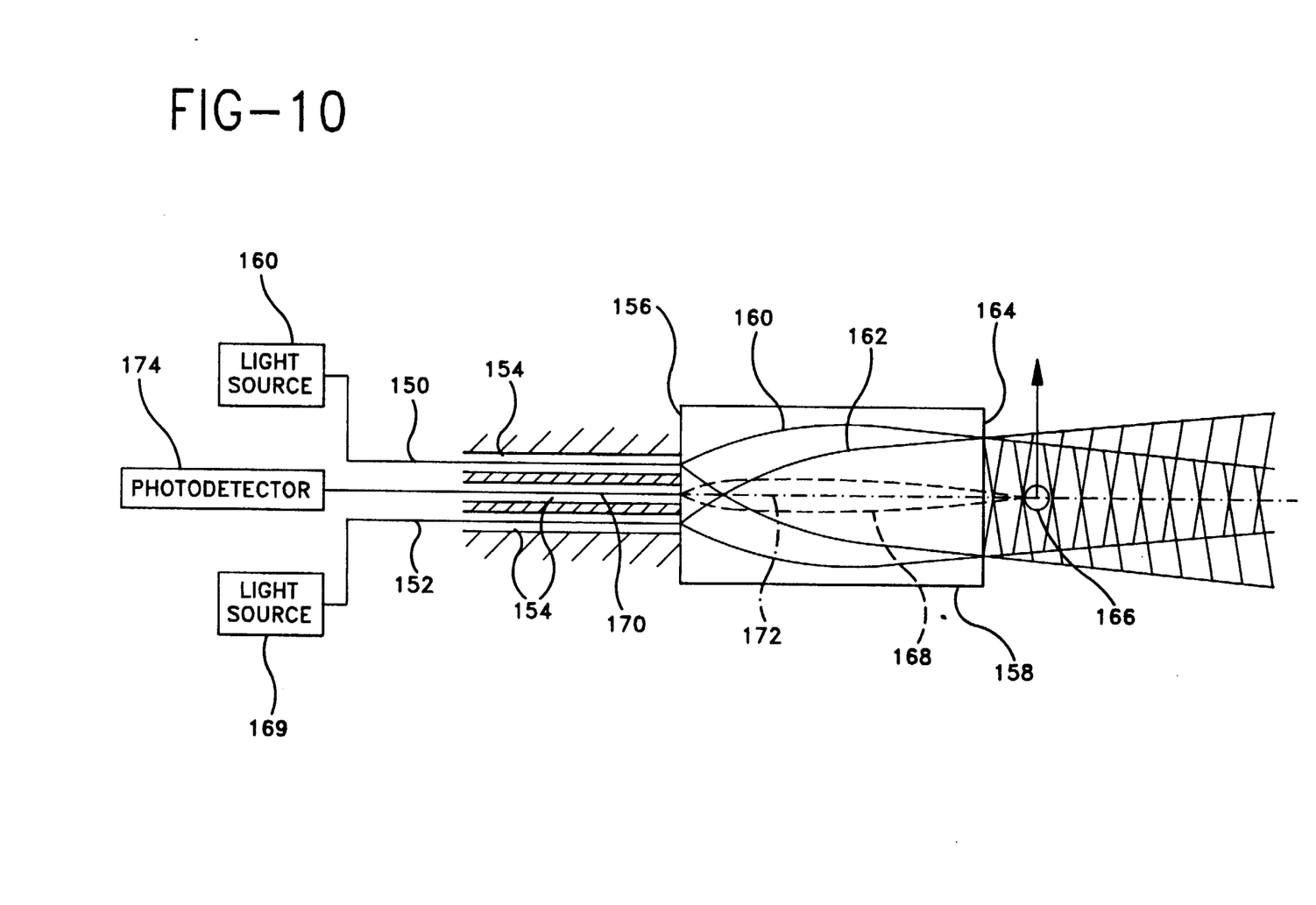
FIG. 10 is an enlarged, schematical illustration of a back scatter fiber optic Doppler anemometer according to the invention.

In FIG. 10, two polarization maintaining, monomode optical fibers 150 and 152 mounted in suitable ferrules 154 are actively aligned to the antireflection coated front surface 156 of a quarter pitch GRIN microlens 158 which delivers two Gaussian laser beams 160 and 162 to the scattering medium. The back surface 164 of the microlens 158 is also antireflection coated. A particle 166 moving parallel to the front surface 164 crosses the two beams 160 and 162, thereby producing a scattered signal 168 comprising two signals corresponding to each of the two incident beams. The scattered signal in the back scatter direction is focussed onto a multimode detection fiber 170 mounted in the ferrule 154 and positioned on the optical axis 172 of the probe and in contact with the front surface 156 of the microlens 158. The system 169 for launching light into the fibers 150 and 152 is as described previously with respect to FIG. 6, as is the detection system 174. This embodiment of the invention is suitable for applications ranging from blood flow to mapping of velocities in supersonic wind tunnels. With two incident beams, one color system, one component of flow, parallel to the surface of the microlens, is measured. The probe could be modified to measure two components of flow by using a two color system. This is achieved by introducing a third transmitting fiber and a second receiver.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A system for determining the physical properties of materials via dynamic light scattering, comprising:
    a probe body;
    a first optical fiber secured to said probe body;
    a second optical fiber secured to said probe body;
    a third optical fiber secured to said probe body;
    a gradient index, quarter pitch microlens including a front face and a back face, said first, second and third optical fibers each including a first free end adjoining said front face of said gradient index microlens and a second free end, the first free ends of said optical fibers being substantially coplanar and substantially colinear;
    means for independently terminating each of the second free ends of the first, second and third optical fibers; and
    photodetecting means connectable to the means for terminating the second free ends of the first, second and third optical fibers.

2. A system as described in claim 1 including means for directing a laser beam into the first optical fiber, and wherein said free end of said second optical fiber is positioned such that at least a portion of any light exiting the first free end of the first optical fiber is reflected by the back face of the microlens into the first free end of the second optical fiber; said first optical fiber being a monomode fiber.

3. A system as described in claim 2 wherein said second optical fiber is a monomode fiber.

4. A system as described in claim 2 wherein said second optical fiber is a multimode fiber.

5. A system as described in claim 2 wherein said free end of said second optical fiber is positioned to provide homodyne detection and said free end of said third optical fiber is positioned to provide self-beating detection.

6. A system as described in claim 5 wherein said front and back faces of said gradient index microlens are antireflection coated.

7. A system as described in claim 2 wherein said front face of said gradient index microlens is antireflection coated while said back face thereof is not antireflection coated.

8. A system as described in claim 2 including means for directing a laser beam into said third optical fiber, the probe body including an optical axis extending through said gradient index microlens, the free end of the second optical fiber being positioned on the optical axis.

9. A system as described in claim 8 wherein said front surface of said gradient index microlens includes an antireflective coating.

10. A system as described in claim 9 wherein said back surface of said gradient index microlens includes an antireflective coating.

11. A system as described in claim 1 wherein said free ends of said first, second and third optical fibers are positioned in the back focal plane of said gradient index microlens.

12. A system as described in claim 1 wherein said second optical fiber is a multimode fiber.

13. A system as described in claim 1 including a fourth optical fiber secured to the probe body and having a first free end adjoining the front face of the gradient index microlens and a second free end terminated independently of the second free ends of the first, second and third optical fibers, the second free ends of the first, second, third and fourth optical fibers being arranged in a substantially colinear, side by side, and adjoining configuration.

14. A system for determining the physical properties of materials via dynamic light scattering, comprising:
   a lensless probe including a first monomode optical fiber having a free end for transmitting a laser light to a scattering medium and a second optical fiber having a free end and defining a scattering angle with respect to the first optical fiber to provide a self-beating receiver of light scattered by a particle adjacent to the free ends of the said first and second optical fibers;
   detecting means connected to said second optical fiber; and
   a probe body, said free ends of said first and second optical fibers being in closely adjoining relation to each other and secured to said probe body.

15. A system as described in claim 14 wherein said second optical fiber is a multimode fiber.

16. A system as described in claim 14 wherein the core of said first monomode fiber is expanded at the free end thereof.

17. A system as described in claim 14 wherein said first and second optical fibers are positioned such that the second optical fiber has a self-beating efficiency parameter $\beta'$ of at least about 0.5.

18. A system as described in claim 14 including a needle having a bore extending therethrough, said first and second optical fibers each extending through said bore of said needle and including free ends extending slightly outside said bore.

19. A system as described in claim 14 wherein the first optical fiber includes a core and a cladding, the core of the first optical fiber being flared at the free end thereof.

20. A system as described in claim 14 wherein the free end of the first optical fiber is oriented in non-parallel relation to the free end of the second optical fiber.

21. A system for determining the physical properties of materials via dynamic light scattering, comprising:
   a first monomode optical fiber including a free end and a microlens integrally formed at the free end thereof;
   a lensless second optical fiber having a selected numerical aperture and a free end positioned so as to act as a self-beating receiver of light scattered by a particle adjacent to the free ends of said first and second optical fibers
   detecting means connected to said second optical fiber; and
   a probe body, said free ends of said first and second optical fibers being in closely adjoining relation to each other and secured to said probe body.

22. A system as described in claim 21 wherein the free end of said first optical fiber is non-parallel to the free end of the second optical fiber.

23. A method as described in claim 21 wherein the first and second optical fibers are positioned such that the second optical fiber has a self-beating efficiency parameter $\beta'$ of at least about 0.5.

24. A method of detecting scattered light from a scattering medium, comprising:
   providing a probe including a probe body, a first optical fiber secured to said probe body, a second optical fiber secured to said probe body, a third optical fiber secured to said probe body, a quarter pitch, gradient index microlens having a front face and a back face, said first, second and third optical fibers including free ends adjoining said front face of said gradient index microlens, the free ends of said optical fibers being arranged in substantially coplanar and colinear relationships;
   directing said probe towards a scattering medium such that said back face of said gradient index microlens faces said scattering medium;
   directing a beam of light towards the scattering medium;
   transmitting light scattered by said scattering medium through each of said optical fibers; and
   analyzing the light passing through each optical fiber independently.

25. A method as described in claim 24 wherein said descend optical fiber is caused to receive light reflected by said back face of said gradient index microlens.

26. A method as described in claim 24 wherein said second optical fiber is caused to receive substantially no light reflected by said back face of said gradient index microlens.

27. A method as described in claim 24 wherein said beam is at least partially reflected by said back face of said gradient index microlens, said second optical fiber receiving substantially no light reflected by said back face, said third optical fiber receiving a substantial amount of light reflected by said back face.

28. A method of detecting scattered light from a scattering medium, comprising:
   providing a probe including a first monomode optical fiber having a lensless free end and a second optical fiber having a lensless free end and constructed to function as a self-beating receiver of light which may be scattered by a particle adjacent to the free ends of said first and second optical fibers;
   causing light to pass through said first optical fiber into a scattering medium; and
   detecting light scattered by said scattering medium and passing into said second optical fiber.

29. A method as described in claim 28 wherein said first optical fiber has an expanded core adjacent the free end thereof, said expanded core reducing the divergence of a light beam exiting the free end of said first optical fiber.

30. A method as described in claim 28 including the step of positioning said free ends of said first and second optical fibers such that said fibers are in adjoining, non-parallel relation.

31. A method as described in claim 28 including the step of providing a needle having a droplet of scattering medium extending from an open end thereof, and positioning said probe such that said first and second optical fibers extend through said needle and said probe is positioned within said droplet.

32. A method as described in claim 28 wherein the first and second optical fibers are positioned such that the second optical fiber has a self-beating efficiency parameter $\beta'$ of at least about 0.5.

* * * * *